US 6,210,874 B1
(10) Patent No.: US 6,210,874 B1
(45) Date of Patent: *Apr. 3, 2001

(12) United States Patent
Lacroix

(54) SYNTHETIC PEPTIDES AND MIXTURES THEREOF FOR DETECTING HIV ANTIBODIES

(75) Inventor: Martial Lacroix, Brossard (CA)

(73) Assignee: Biochem Immunosystems, Inc., Quebec (CA)

(*) Notice: Subject to any disclaimer, the term of this patent is extended or adjusted under 35 U.S.C. 154(b) by 0 days.

This patent is subject to a terminal disclaimer.

(21) Appl. No.: 08/432,520

(22) Filed: May 1, 1995

Related U.S. Application Data

(60) Continuation of application No. 08/077,085, filed on Jun. 16, 1993, now abandoned, which is a division of application No. 07/549,964, filed on Jul. 9, 1990, now Pat. No. 5,241,047, which is a continuation-in-part of application No. 07/281,205, filed on Dec. 8, 1988, which is a continuation-in-part of application No. 07/185,518, filed on Apr. 22, 1988, now abandoned, which is a continuation-in-part of application No. 07/148,821, filed on Jan. 27, 1988.

(51) Int. Cl.[7] ...................................................... C12Q 1/70

(52) U.S. Cl. ............................... 435/5; 530/317; 530/324

(58) Field of Search .................................. 530/324, 317; 514/12; 435/5

(56) References Cited

U.S. PATENT DOCUMENTS

| | | | |
|---|---|---|---|
| 4,629,783 | 12/1986 | Cosand | 435/5 |
| 4,735,896 | 4/1988 | Wang | 435/5 |
| 4,772,547 | 9/1988 | Heimer | 435/5 |
| 4,812,556 | 3/1989 | Vahlne | 530/324 |
| 4,879,212 | 11/1989 | Wang | 435/5 |
| 4,957,737 | 9/1990 | Heimer | 424/88 |
| 5,001,049 | 3/1991 | Klein | 435/5 |
| 5,241,047 | * 8/1993 | Lacroix | 530/324 |
| 5,260,189 | * 11/1993 | Formoso et al. | 435/5 |

FOREIGN PATENT DOCUMENTS

| | | | |
|---|---|---|---|
| 0219106 | 4/1987 | (EP) | 435/5 |
| 0231914 | 8/1987 | (EP) | 435/5 |
| 0233045 | 8/1987 | (EP) | 435/5 |
| 0247557 | 12/1987 | (EP) | 435/5 |
| 2593189 | 7/1987 | (FR) . | |
| 2593190 | 7/1987 | (FR) . | |
| 2593922 | 8/1987 | (FR) . | |
| 2594229 | 8/1987 | (FR) . | |
| 2596063 | 9/1987 | (FR) . | |
| 2597500 | 10/1987 | (FR) . | |
| 2610632 | 4/1988 | (FR) . | |
| 2614025 | 10/1988 | (FR) . | |
| 87/04185 | 4/1989 | (SE) . | |
| WO/86/06414 | 11/1986 | (WO) | 435/5 |
| 87/04459 | 7/1987 | (WO) . | |
| WO/87/06005 | 10/1987 | (WO) | 435/5 |
| 89/03844 | 5/1989 | (WO) . | |

OTHER PUBLICATIONS

Allizon et al. "Genetic variability of the IAFS Virus: Nucleotide Sequence . . . " Cell, 46 (Jul. 1986), pp. 63–74.

(List continued on next page.)

Primary Examiner—Robert D. Budens
(74) Attorney, Agent, or Firm—Nixon & Vanderhye

(57) ABSTRACT

Cyclic peptides of the general formulae:

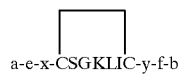

(I)

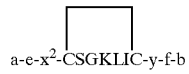

(III)

wherein x represents an amino acid sequence from position 585 to 604 (gp41-HIV-1) with at least one of a lysine at position 586 or a lysine at both positions 585 and 586; $x^2$ represents an amino acid sequence from position 585 to 604 (gp41-HIV-1); y represents an amino acid sequence from position 612 to 629 (gp41-HIV-1); e and f represent one or more epitopes included in the amino acid sequence extending from 586 to 629 (gp41-HIV-1) or from 578 to 613 (gp36-HIV-2); and a and b represent the amino and carboxy terminals, respectively, as well as substituents effective to make the peptide more useful as an immunodiagnostic. Peptides of formula III have one or both of e and f present. Also provided are peptides of the general formulae:

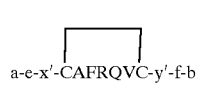

(II)

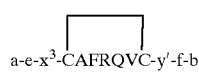

(IV)

wherein $x^1$ represents an amino acid sequence from position 577 to 596 (gp36-HIV-2) with at least one of a lysine at position 578 or a lysine at both positions 577 and 578; $x^3$ represents an amino acid sequence from position 577 to 596 (gp36-HIV-2); $y^1$ represents an amino acid sequence from position 604 to 613 (gp36-HIV-2); e and f represents one or more epitopes included in the amino acid sequence from 578 to 613 (gp36-HIV-2) or 586 to 629 (gp41-HIV-1); and a and b are as defined above. Peptides of formula IV have one or both of e and f present. These peptides are useful in detecting HIV-1 and HIV-2 antibodies.

3 Claims, No Drawings

OTHER PUBLICATIONS

Bologresi, D. Tibtech, vol. 8 (1990), pp. 40–45. Dayhoff. Atlas of Protein Sequence & Structure, vol. 5, (1972), pp. 89–99.

Gallaher. "Detection of a fusion peptide sequence in the transmembrane . . . ", Cell, 50 (1987), pp. 327–328.

Gnann et al. "Fine mapping of an immunodominant domain in the . . . " J. of Virology, 61 (8) (Aug. 1987), pp. 2639–2641.

Gnann et al. "Diagnosis of AIDS by using a 12–amino acid . . . " J. of Inf. Dis., vol. 156, No. 2 (Aug. 1987), pp. 261–267.

Gnann et al. "Synthetic peptide immunoassay distinguishes HIV type . . . ", Science, vol. 237 (Sep. 1989), pp. 1346–1349.

Ratner et al. "Complete nucleotide sequence of the AIDS virus HTLV–III", Nature, vol. 313, (Jan. 1985), pp. 275–283.

Wang et al. "Detection of antibodies of human T–lymphotropic . . . " Proc. Natl. Acad. Sci. USA, vol. 83 (Aug. 1986), pp. 6159–6163.

* cited by examiner

SYNTHETIC PEPTIDES AND MIXTURES THEREOF FOR DETECTING HIV ANTIBODIES

This is a continuation of application Ser. No. 08/077,085, filed Jun. 16, 1993, now abandoned, which is a division of application Ser. No. 07/549,964, filed Jul. 9, 1990, now U.S. Pat. No. 5,241,047; which is a CIP of application Ser. No. 07/281,205, filed Dec. 8, 1988, which is a CIP of application Ser. No. 07/185,518, filed Apr. 22, 1988, now abandoned; which is a CIP of application Ser. No. 07/148,821, filed Jan. 27, 1988.

FIELD OF THE INVENTION

The present invention relates to novel cyclic peptides and combinations thereof alone and with linear and cyclic peptides for detecting HIV antibodies.

BACKGROUND OF THE INVENTION

Acquired Immune Deficiency Syndrome (AIDS), AIDS related complex (ARC) and pre-AIDS are thought to be caused by a retrovirus, the Human Immunodeficiency Virus (HIV). The first AIDS related virus, HIV-1 (also known as HTLV-III, LAV-1 and ARV) has been well characterized. Another pathogenic human retrovirus named HIV-2 (formerly LAV-2) has now been isolated from West African patients with AIDS. See, e.g., WO 87/04459. HIV-2 has recently been shown (Guyader et al. Nature 326 662–669, 1987) to share a number of conserved sequences with HIV-1 and the Simian Immunodeficiency Viruses (SIV).

Even though other numbering systems are used in the art, for ease of understanding and comparison we have adopted herein the amino acid numbering system of Ratner et al., Nature, 313, 277–284, 1985 for the HIV-1 proteins and that of Guyader et al., Nature 326, 662–669 (1987) for the HIV-2 proteins. The amino acids in the peptides of this invention are designated by the single letter code as follows: ala=A, arg=R, asn=N, asp=D, cys=C, gln=Q, glu=E, gly=G, his=H, ile=I, leu=L, lys=K, met=M, phe=F, pro=P, ser=S, thr=T, trp=W, tyr=Y and val=V.

The initial immunodiagnostic tests for the detection of antibodies in the serum of patients infected with HIV-1 utilized the whole virus as antigen. Second generation tests made use of polypeptide sequences obtained by the recombinant DNA methodology. Cabradilla et al. Bio/Technology 4 128–133 (1985) and Chang et al. Bio/Technology 3, 905–909 (1985), for example, refer to bacterially synthesized viral protein fragments of 82 and 102 amino acid residues, respectively. EPA 202314 and 114243 refer to recombinant polypeptides spanning regions of gp41 and gp120 that are immunoreactive alone or in mixtures. Shoeman et al., Anal. Biochem. 161, 370–379 (1987) refers to several polypeptides from gp41 that are immunoreactive with antibodies present in sera from patients infected with HIV-1. None of the above assay procedures is, however, totally acceptable. Their lack of sensitivity is a critical shortcoming. It may permit blood containing virus to escape detection and thereby potentially result in the infection of blood product receivers and continued infectivity by undiagnosed AIDS carriers. Their lack of specificity (false positives) is also a problem—healthy individuals are told they may have AIDS. Such false positive may be caused by impurities. They may also be caused by shared epitopes with viruses unrelated to AIDS present in these antigen preparations. In this regard, Gallaher, Cell 50 327–328, 1987 has reported that a region of gp41 of HIV-1 shares a sequence of five adjacent amino acid residues with the respiratory syncytial virus and of four equally distributed amino acids of the measles virus F1 glycoprotein. Thus, even highly purified recombinant polypeptides containing this region, or any other common regions yet to be discovered, could potentially be responsible for false positives and the attendant unacceptable specificity. Finally, these prior art assays do not permit detection of very low levels of HIV antibodies. This disadvantages the assays in terms of their ability to detect AIDS infections at a very early stage, thereby delaying the start of treatment and permitting the possible spread of infection by blood samples and other body fluids before effective detection of AIDS infection.

In an attempt to solve these problems, diagnostic means and methods employing shorter HIV antigens are now being developed. Empirical methods to identify peptide sequences corresponding to unique and highly conserved epitopes of the HIV viruses are also now available. These methods are, for example, capable of assisting in the selection of short amino acid sequences which are more likely to be exposed on the surface of the native protein and thus useful as assay tools (for a review see Hopp and Woods, J. Immunol. Met. 88, 1–18, 1986). Although somewhat useful, these methods are no more than indicative. Nonetheless, they have been applied to identify epitopes present on the surface of viruses responsible for AIDS. For example, U.S. Pat. No. 4,629,783, International Patent Appl. PCT/US86/00831 and EPA 303224 refer to various synthetic peptides from the p18, p25, gp41 and gp120 proteins. These peptides are advantaged by the relative ease and lower cost with which they can be prepared and more importantly because of the reduced risk of obtaining false positives with them due to impurities or the presence of shared epitopes with viral proteins not related to AIDS.

While these smaller peptides are advantaged in terms of specificity over the earlier recombinant polypeptide and whole virus approaches to the diagnosis of AIDS infections, they have been less than satisfactory in terms of overall sensitivity, perhaps because the synthesized epitope is not able to assume and maintain a conformation that is recognized by the AIDS antibodies. Although the number of serum samples tested in each of these cases is very limited, specificity (few if any false positives) was found to be very high (95%–100%) with the small synthetic peptides but the overall sensitivity varied between 80% and 100%. In fact, in the only example where 100% sensitivity was attained only ten samples were tested. For example, Smith et al., J. Clin. Microbiol. 25 1498–1504, 1987 refers to two overlapping peptides, E32 and E34, that are highly immunoreactive. No false positives, out of 240 seronegative specimens, were obtained but the peptides missed three seropositive samples out of 322 (sensitivity of 99.1%). Wang et al. (Proc. Natl. Acad. Sci 83, 6159–6163, 1986) refers to a series of overlapping peptides (including amino acid residues of Smith's E32 and E34 peptides) among which one 21-mer peptide showed 100% specificity and 98% sensitivity (out of 228 seropositive samples taken from patients with AIDS, 224 were found positive with this peptide). And U.S. patent application 120,027, filed Nov. 13, 1987 refers to a short synthetic peptide spanning residues 606 to 620 (SGKLICTTAVPWNAS) of gp41 (HIV-1). This peptide is said to be immunoreactive with antibodies of patients infected by the AIDS viruses. The specificity was also excellent (63/63) but 6 seropositive specimens out of 57 confirmed positive could not be detected (sensitivity of 89%).

Gnann et al. (J. Virol. 61, 2639–2641, 1987 and J. Infec. Dis 156, 261–267, 1987) also refer to a series of overlapping peptides from a suspected immunodominant region of gp41 (HIV-1). Gnann et al. concluded that cys-605 was essential for the immunoreactivity of that segment of the gp41-(HIV-1) protein. They reported that a peptide having the sequence SGKLIC (606–611) was not immunoreactive with any of the 22 HIV-1 positive sera tested, while the addition of the cysteine residue to the N-terminus restored some immunoreactivity, 21 of 44 sera reacted with the 7-mer peptide (48% sensitivity).

Gnann et al. (J. Virol) also speculated that the cysteine residues at positions 605 and 611 of gp41 (HIV-1) might play a role in the antigenic conformation of this region perhaps by the formation of a cyclic structure via disulfide bonding. However, Gnann et al. never demonstrated that they did have a synthetic peptide wherein the two cysteine groups were linked by disulfide bonds.

Although Gnann et. al refers to peptides which are useful in identifying HIV-1 antibodies, even its peptides lack 100% sensitivity. For example, Gnann et al. (J. Virol. 61, 2639–2641, (1987)) report that while their 600–611 amino acid sequence detected 22 out of 22 positive sera, they also reported that similar tests carried out at the Centers for Disease Control, Atlanta, Ga. with the same 12-amino acid sequence (600–611) missed 1 out of 79 positive sera. And Gnann et al. in J. Infect. Dis. 156, 261–267, 1987 reported that the same 12-amino acid sequence was reactive with 131 out of 132 HIV-1 infected patients from the United States.

Gnann et al. Science 237, 1346–1349, 1987 reports a short linear synthetic peptide spanning residues 592 to 603 of gp42 (HIV-2) that contains two cysteines in a region homologous to the 605–611 region of gp41(HIV-1). This peptide reacted with 5 out of 5 sera taken from HIV-2 infected patients.

Other peptides containing amino acids 605–611 of gp41 of (HIV-1) are also referred to in the art. WO 86/06414 refers to peptide X(39), which is encoded by the region from about bp 7516 through bp 7593, and peptide XIII(79) which is encoded by the region extending from about bp 7543 through bp 7593, both containing the 7-amino acid sequence 605–611. These peptides are reported to be linear and no formation of cyclic structures is suggested. WO 87/06005 reports that a series of synthetic peptides encompassing the Cys(605)–Cys(611) residues of the HIV-1 envelope glycoprotein (gp41) undergo a series of spontaneous oxidative transformations upon solubilization in neutral or basic aqueous buffer. It speculates that as a result, the peptides when used in ELISAs are a random mixture of linear monomer, cyclic monomer, linear or cyclic dimers and linear polymers of various lengths. The application did not actualy demonstrate the presence of cyclic components and did not characterize the other various dimers and polymers possibly present. Moreover, it speculates that the polymer forms are the most important components for ELISA reactivity.

In addition to perhaps being complex mixtures of various oxidative forms of the peptide, the prior art peptides referred to above do not permit as early detection of AIDS infection as would be desirable. For example, Gnann et al. (J. Virol) reports that when the HIV-1 positive sera are diluted by a factor exceeding 500, some of these diluted sera are found to be negative thus indicating a low sensitivity of the peptide for early HIV detection.

These problems have been addressed by employing peptides that have been chemically cyclized to form a disulfide bridge between the relevant cysteines. E.g., M. Lacroix et al., Comparative Performance of Cyclic Versus Linear Peptides In An ELISA For HIV-1 And HIV-2 Specific Antibodies, No. 3147, June 1989 AIDS Conference, Montreal, Canada; and WO 89/03344. This invention is directed to improvements in such cyclic peptides.

SUMMARY OF THE INVENTION

In accordance with the present invention, there is provided a novel series of peptides which are particularly adapted for detecting 100% of HIV-1 and HIV-2 antibodies and which are capable of detecting such antibodies even when present in very low levels in sera.

More specifically, the novel peptides of the present invention are selected from substantially pure peptides of formulae I or II:

(I)

a-e-x-CSGKLIC-y-f-b 605 611 wherein:

x is independently selected from one of the following amino acid sequence analogs of the amino acid sequence of gp41-HIV-1:

KILAVERYLKDQQLLGIWG- (586–604)

KKILAVERYLKDQQLLGIWG- (585–604), amino acid sequences corresponding thereto, which sequences are derived from homologous regions of other HIV-1 isolates, and amino acid sequences differing from the above as a result of conservative substitutions, such amino acid sequences being characterized by at least one of a lysine at position 586 or a lysine at both positions 585 and 586;

y, if present, is independently selected from the group consisting of:

—T

—TT

—TTA

—TTAV

—TTAVP

—TTAVPW

—TTAVPWN

—TTAVPWNA

—TTAVPWNAS

—TTAVPWNASW

—TTAVPWNASWS

—TTAVPWNASWSN

—TTAVPWNASWSNK

—TTAVPWNASWSNKS

—TTAVPWNASWSNKSL

—TTAVPWNASWSNKSLE

—TTAVPWNASWSNKSLEQ

—TTAVPWNASWSNKSLEQI, amino acid sequences corresponding thereto, which sequences are derived from homologous regions of other HIV-1 isolates, and amino acid sequences differing from the above as a result of conservative substitutions;

e and f, if present, are independently selected from the group consisting of an amino acid sequence of any one of the epitopes of the region spanning amino acids 586 to 629 of gp41 of HIV-1 or of the region spanning amino acid sequence 578 to 613 of gp36 of HIV-2, amino acid sequences corresponding thereto and being derived from homologous regions of other HIV-1 or HIV-2 isolates, amino acid sequences differing from the above as a result of conservative substitutions, and any combination of these epitopes;

a is an amino terminus or a substitutent effective as a coupling agent and/or to make the peptide more useful as an immunodiagnostic reagent without changing its antigenic properties; and b is a carboxy terminus or a substituent effective as a coupling agent and/or to make the peptide more useful as an immunodiagnostic reagent without changing its antigenic properties; and $$a\text{-}e\text{-}x^1\text{-}\overset{\boxed{\phantom{xx}}}{CAFRQVC}\text{-}y'\text{-}f\text{-}b \quad (II)$$
$$\phantom{a\text{-}e\text{-}x^1\text{-}}597\phantom{CAFRQ}603$$

wherein:

$x^1$ is independently selected from one of the following amino acid sequence analogs of the amino acid sequence of gp36-HIV-2:

KVTAIEKYLQDQARLNSWG (578–596)
KKVTAIEKYLQDQARLNSWG (577–596), amino acid sequences corresponding thereto, which sequences are derived from homologous regions of other HIV-2 isolates and amino acid sequences differing from the above as a result of conservative substitutions, such sequences being characterized by at least one of a lysine at position 578 or a lysine at both positions 577 and 578;

$y^1$, if present, is independently selected from the group consisting of:

——H
——HT
——HTT
——HTTV
——HTTVP
——HTTVPW
——HTTVPWV
——HTTVPWVN
——HTTVPWVND
——HTTVPWVNDS, amino acid sequences corresponding thereto, which sequences are derived from homologous regions of other HIV-2 isolates, and amino acid sequences differing from the above as a result of conservative substitutes; and e, f, a and b are as defined above.

In another embodiment, the novel peptides of this invention are selected from substantially pure peptides of the formulae III and IV:

$$a\text{-}e\text{-}x^2\text{-}\overset{\boxed{\phantom{xx}}}{CSGKLIC}\text{-}y\text{-}f\text{-}b \quad (III)$$
$$\phantom{a\text{-}e\text{-}x^2\text{-}}605\phantom{CSGK}611$$

wherein $x^2$, if present, is independently selected from the group consisting of:

G——
WG——
IWG——
GIWG——
LGIWG——
LLGIWG——
QLLGIWG——
QQLLGIWG——
DQQLLGIWG——
KDQQLLGIWG——
LKDQQLLGIWG——
YLKDQQLLGIWG——
RYLKDQQLLGIWG——
ERYLKDQQLLGIWG——
VERYLKDQQLLGIWG——
AVERYLKDQQLLGIWG——
LAVERYLKDQQLLGIWG——
ILAVERYLKDQQLLGIWG——
RILAVERYLKDQQLLGIWG—— , amino acid sequences corresponding thereto, which sequences are derived from homologous regions of other HIV-1 isolates, and amino acid sequences differing from the above as a result of conservative substitutions; and y, e, f, a and b are as previously defined, one or both of e or f being present; and $$a\text{-}e\text{-}x^3\text{-}\overset{\boxed{\phantom{xx}}}{CAFRQVC}\text{-}y'\text{-}f\text{-}b \quad (IV)$$
$$\phantom{a\text{-}e\text{-}x^3\text{-}}597\phantom{CAFRQ}603$$

wherein $x^3$, if present, is independently selected from the group consisting of:

G——
WG——
SWG——
NSWG——
LNSWG——
RLNSWG——

-continued
ARLNSWG—
QARLNSWG—
DQARLNSWG—
QDQARLNSWG—
LQDQARLNSWG—
YLQDQARLNSWG—
KYLQDQARLNSWG—
EKYLQDQARLNSWG—
IEKYLQDQARLNSWG—
AIEKYLQDQARLNSWG—
TAIEKYLQDQARLNSWG—
VTAIEKYLQDQARLNSWG—
RVTAIEKYLQDQARLNSWG—, amino acid sequences corresponding thereto, which sequences are derived from homologous regions of other HIV-2 isolates, and amino acid sequences differing from the above as a result of conservative substitutions; and $y^1$, e, f, a and b are as previously defined, one or both of e or f being present.

A particularly preferred peptide of formula I is BCH-408 which has the following sequence:

a-KILAVERYLKDQQLLGIWGCSGKLICTTAVPWNASGKLI-b
586                        605    611        619

This peptide incorporates at the f position 619 the amino acid sequence of the epitope located at position 606–610 (SGKLI) of gp41 of HIV-1 and at position 586 a lysine.

A particularly preferred peptide of formula II is BCH-417 which has the following sequence:

a-KVTAIEKYLQDQARLNSWGCAFRQVCHTTVPWVNDSAFRQV-b.
578                       597     603          613

This peptide incorporates at the f position 613 the amino acid sequence of the epitope located at position 598–602 (AFRQV) of gp36 of HIV-2 and at position 578 lysine.

DETAILED DESCRIPTION OF THE INVENTION

Selection of Peptides for Synthesis

The peptides of this invention were synthesized on the basis of published amino acid sequences of HIV-1 and HIV-2. However, it should be understood that sequences derived from the homologous regions of other HIV-1 or HIV-2 isolates can be used without departing from the scope of this invention.

Epitopes in these native sequences were chosen for use as e and f, in the peptides of this invention using various physicochemical principles that aid in predicting which portions of a polypeptide are most likely to be surface oriented and therefore immunogenic. These include the hydrophilicity plots of Hopp and Woods (Proc. Natl. Acad. Sci. 78, 3824–3828, 1981), and a similar approach by Kyte and Doolittle (J. Mol. Biol. 157, 105–132, 1982). Also, the empirical prediction of protein conformation (Chou and Fasman, Ann. Rev. Biochem. 47, 251–276, 1978) is a useful guide in predicting which parts of the polypeptide are likely to be immunogenic.

The e and f epitopes of the peptides of this invention include, but are not limited to, WGCAF (identified by Norrby et al., AIDS Research and Human Retroviruses, Vol. 5, No. 5, 1989); KD, SGKL, and LEDQ (identified by Norrby et al., AIDS, Vol. 3, No. 1 (1989); LKDQ, CSGKLI, and IWG (identified by Mathiesen et al., Immunology, 67 1–7 (1989); and ARILAVERYLKD, and SGKLICTTAVP-WNAS (identified by Dopel et al., Jol. of Vir. Meth., 25 167–178 (1989).

It is also within the scope of this invention to modify the peptides of this invention, in order to make them more useful as immunodiagnostic reagents without changing their antigenic properties. Such changes include:

addition of a cysteine residue at the amino or carboxy terminus in order to facilitate coupling of the peptide to a carrier protein with heterobifunctional cross-linking reagents such as sulfosuccinimidyl-4(p-maleimidophenyl)butyrate, a preferred reagent for effecting such linkages;

addition of certain amino acids at the amino or carboxy terminus to facilitate linking of peptides to each other, for coupling to a support or larger peptide or for modifying the physical or chemical properties of the peptide. Such changes may be effected, for example, by additions of tyrosine, glutamic acid or aspartic acid, which can be used as linkers via an esterification reaction, and lysine which can be connected by Schiff base or amide formation; and derivatization by amino terminal acylation, thioglycolic acid amidation, and carboxy terminal amidation, e.g. using ammonia, methylamine. These modifications result in changes in net charge on the peptide and can also facilitate covalent linking of the peptide to a solid support, a carrier or another peptide. These modifications are not likely to result in immunoreactivity changes to the peptide.

The peptides of this invention may also be modified by various changes such as insertions, deletions and substitutions, either conservative or nonconservative where such changes might provide for certain advantages in their use. These changes include preferably the following conservative changes: gly, ala; val, ile, leu; asp, glu; asn, gln; ser, thr; lys, arg; phe, tyr; ala, ser; ala, thr; ala, val; ala, pro; ala, glu; leu, gln; gly, phe; ile, ser; and ile, met. Methionine, an amino acid which is prone to spontaneous oxidation, can also usually be replaced by norleucine without changing antigenicity.

It may also be convenient to add a "tail" consisting of a small number (1–10) of hydrophobic amino acids to the peptides of this invention. Such tails may facilitate passive adsorption of a peptide to a solid support. This modification can be made at either the COOH or $NH_2$ termini. The preferred addition is phe-ala-phe-ala-phe.

In accordance with this invention, the preferred cyclic peptides of formula I are those having x, y, e and f defined as follows:
x: KILAVERYLKDQQLLGIWG, y: TTAVPWNAS, e and f not present (BCH-87ck);
x: KKILAVERYLKDQQLLGIWG, y: TTAVPWNAS, e and f not present (BCH-266); and
x: KILAVERYLKDQQLLGIWG, y: TTAVPWNA,
f: SGKLI and e not present (BCH-408), BCH-408 being the most preferred.

The preferred cyclic peptides of formula II are those having $x^1$, $y^1$, e and f defined as follows:

$x^1$: KVTAIEKYLQDQARLNSWG, $y^1$: HTTVPWVNDS and e and f not present (BCH-202ck);

$x^1$: KKVTAIEKYLQDQARLNSWG, $y^1$: HTTVPWVNDS and e and f not present (BCH-265); and $x^1$: KVTAIEKYLQDQARLNSWG, $y^1$: HTTVPWVNDS and f: AFRQV and e not present (BCH-417), BCH-417 being the most preferred.

TABLE I provides the full amino acid sequences of these preferred peptides (disregarding possible a and b):

chain is preferably 9-fluorenylmethyloxycarbonyl (Fmoc), although any other suitable protecting group may be employed as long as it does not degrade under the coupling conditions and is readily removable selectively in the presence of any other protecting groups already present in the growing molecule.

The criteria for selecting protecting groups for the side chain amino acids are: (a) stability of the protecting group to the various reagents under reaction conditions selective for the removal of the α-amino protecting group at each step of the synthesis: (b) retention of the protecting group's strategic properties (i.e. not be split off under coupling conditions)

TABLE 1

Peptide sequences

HIV-1:

BCH-87ck:
KILAVERYLKDQQLLGIWGCSGKLICTTAVPWNA

BCH-266:
KKILAVERYLKDQQLLGIWGCSGKLICTTAVPWNA

BCH-408:
KILAVERYLKDQQLLGIWGCSGKLICTTAVPWNASGKI

HIV-2:

BCH-202ck:
KVTAIEKYLQDQARLNSWGCAFRQVCHTTVPWVNDS

BCH-265:
KKVTAIEKYLQDQRELNSWGCAFRQVCHTTVPWVNDS

BCH-417:
KVTAIEKYLQDQARLNSWGCAFRQVCHTTVPWVNDSAFRQV

Preparation of Linear and Cyclic Peptides

The peptides of this invention are preferably prepared using conventional solid phase synthesis. However, other well known methods of peptide synthesis may also be used. The resin support is any suitable resin conventionally employed in the art for solid phase preparation of polypeptides, preferably p-benzyloxyalcohol polystyrene and p-methylbenzydrylamine resin. Following the coupling of the first protected amino acid to the resin support, the amino protecting group is removed by standard methods conventionally employed in the art of solid phase peptide synthesis. After removal of the amino protecting group, remaining α-amino protected and, if necessary, side chain protected amino acids are coupled, sequentially, in the desired order to obtain the product. Alternatively, multiple amino acid groups may be coupled using solution methodology prior to coupling with the resin-supported amino acid sequence.

The selection of an appropriate coupling reagent follows established art. For instance, suitable coupling reagents are N,N'-diisopropylcarbodiimide or N,N'-dicyclohexylcarbodiimide (DCC) either alone or preferably in the presence of 1-hydroxybenzotriazole. Another useful coupling procedure makes use of preformed symmetrical anhydrides of protected amino acids.

The necessary α-amino protecting group employed for each amino acid introduced onto the growing polypeptide and (c) removability of the protecting group upon conclusion of the polypeptide synthesis and under conditions that do not otherwise affect the polypeptide structure.

The fully protected resin-supported peptides are cleaved from the p-benzyloxy alcohol resin with 50 to 60 percent solution of trifluoroacetic acid in methylene chloride for 1 to 6 hours at room temperature in the presence of appropriate scavengers such as anisole, thioanisole, ethyl methyl sulfide, 1,2-ethanedithiol and related reagents. Simultaneously, most acid labile side-chain protecting groups may then be removed. More acid resistant protecting groups are removed by HF treatment.

Cyclic peptides of this invention are prepared by the direct oxidative conversion of protected or unprotected SH-groups to a disulfide bond by following techniques generally known in the art of peptide synthesis. The preferred method involves the direct oxidation of free SH-groups with potassium ferricyanide. Such cyclic peptides are believed to assume a more rigid conformation which may favor binding to HIV antibodies.

Peptide Mixtures and Polymers

Within the scope of this invention are larger peptides formed by the covalently linking of one or more peptides of this invention. Polymers (both homo and co) of these peptides are also envisioned.

Also within the scope of the present invention are other cyclic and mixtures of the cyclic peptides of this invention and other cyclic and linear HIV derived peptides. These mixtures have surprisingly been found to provide high sensitivity detection of HIV-1 and HIV-2 antibodies present in serially diluted serum samples and in seroconversion panels (HIV-1). Also it has been found that these mixtures provide a high level of specificity resulting in a minimal number of false positives.

Such mixtures comprise at least one cyclic peptide of the general formulae I or III (preferably BCH-87ck, BCH-266 or BCH-408 and more preferably BCH-408) in combination with at least one cyclic peptide of the general formulae II or IV (preferably BCH-202ck, BCH-265 or BCH-417 and more preferably BCH-417).

HIV Antibody Detection

The peptides and the peptide mixtures of the present invention are useful as diagnostic reagents for the detection of AIDS-associated antibodies in accordance with methods well-known in the art. These include ELISA, hemagglutination, single-dot and multi-dot methods and assays. The main advantage of the present peptides in the determination of antibodies against AIDS resides in their specificity and high sensitivity, and particularly their ability to detect the presence of very low levels of AIDS infection, when compared with known antigens used so far.

According to one method for the determination of antibodies against HIV-1 or HIV-2, the so-called "Western Blotting" analysis is used [Towbin, H., Staehelin, T. and Gordon, J., Proc. Nat. Acad. Sci. U.S.A. 76, 4350–4354 (1979)]. According to this technique a peptide or peptides of the present invention is (or are) applied to nitrocellulose paper. The nitrocellulose paper is saturated and then treated with the serum to be tested. After washing, the nitrocellulose paper is treated with an anti-human IgG labeled with an enzyme. The enzymatic activity is then determined by a suitable substrate. Of course, other labels, like radioactive or fluorescence labels, may be used.

A preferred convenient and classical technique for the determination of antibodies against HIV-1 or HIV-2 using a peptide or a peptide mixture of the present invention is an enzyme-linked immunosorbent assay (ELISA). In this assay, for example, a peptide, peptide mixture or combination of the present invention is adsorbed onto, or covalently coupled to, the wells of a microtiter plate. The wells are then treated with the sera or analyte to be tested. After washing, anti-human IgG or antihuman IgM labeled with peroxidase is added to the wells. The determination of the peroxidase is performed with a corresponding substrate, e.g., with o-phenylene diamine. Without departing from the usefulness of the illustrative assay, the peroxidase can be exchanged by another label, e.g., by a radioactive, fluorescence chemiluminescence or infra-red emitting label.

In the ELISA test, it is possible to use individual peptides or a combination thereof. The latter is preferable since it allows one to combine the most effective peptides for detecting antibodies while at the same time excluding those that contribute to false responses. It was discovered during the course of these studies that some serum samples gave correct positive results with mixtures of peptides while giving equivocal responses with individual peptides as antigen. Thus the most preferred test for HIV-1 and HIV-2 antibodies is achieved in accordance with this invention using a combination of peptide antigens.

Another method for the determination of antibodies against HIV-1 or HIV-2 with the peptides or mixture of peptides of this invention is an enzyme immunological test according to the so-called "Double-Antigen-Sandwich-Method". This method is based on the work of Maiolini as described in Immunological Methods 20, 25–34 (1978). According to this method, the serum or other analyte to be tested is contacted with a solid phase on which a peptide or mixture of peptides of the present invention has been coated (capture layer) and with a peptide or a peptide mixture of the present invention which is labeled with peroxidase (probe layer). The immunological reaction can be performed in one or two steps. If the immunological reaction is performed in two steps, then a washing step is preferably performed between the two incubations. After the immunological reaction or reactions, a washing step may also be performed. Thereafter, the peroxidase is determined with a substrate, e.g., with o-phenylene diamine. Other enzymes and chromogens, including those already described can also be employed in this assay.

Suitable solid phases are organic and inorganic polymers, such as amylases, dextrans, natural or modified celluloses, polyethylenes, polystyrenes, polyacrylamides, agaroses, magnetites, porous glass powders, polyvinyldiene fluoride (kynar) and latex, the inner wall of test vessels e.g., test tubes, titer plates or cuvettes of glass or articifial material as well as the surface of solid bodies, e.g., rods of glass and artificial material, rods with terminal thickening, rods with terminal lobes or lamallae. Spheres of glass and artificial material are especially suitable solid phase carriers.

The peptides and mixtures of peptides of the present invention are not only useful in the determination of antibodies against HIV-1 or HIV-2, but also indirectly for the determination of HIV-1 or HIV-2 itself since these peptides either free, polymerized or conjugated to an appropriate carrier are useful in eliciting antibodies, in particular monoclonal antibodies, against HIV-1 or HIV-2. Such antibodies can be produced by injecting a mammalian or avian animal with a sufficient amount of a peptide or mixture of peptides of the present invention and recovering said antibodies from the serum of said animals. Suitable host animals for eliciting antibodies include mammals such as rabbits, horses, goats, guinea-pigs, rats, mice, cows, sheep, etc..

Various methods which are generally known can be employed using the peptides of this invention or mixtures thereof in the quantitative determination of HIV-1 or HIV-2 infection. In one such procedure known amounts of a serum sample to be assayed, radiolabeled cyclic peptide of the present invention or mixtures of those peptides and unlabeled peptide or mixture of peptides of the present invention are mixed together and allowed to stand. The antibody/antigen complex is separated from the unbound reagents by procedures known in the art, i.e., by treatment with ammonium sulfate, polyethylene glycol, a second antibody either in excess or bound to an insoluble support, dextran-coated charcoal and the like. The concentration of the labeled peptide or mixture of peptides of the present invention is determined in either the bound or unbound phase and the HIV-1 or HIV-2 content of the sample can then be determined by comparing the level of labeled component observed to a standard curve in a manner known 'per se'.

Another suitable quantitative method is the "Double-Antibody-Sandwich-Assay". According to this assay the sample to be tested is treated with two different antibodies raised against a peptide of this invention or mixture thereof using different animals, e.g. sheep or rabbits. Alternatively, monoclonal antibodies may be prepared using the well-known Koehler and Milstein technique for producing monoclonal antibodies. In order to distinguish monoclonal antibodies which are directed against the same antigen, but against different epitopes, the method of Stähli et al. [J. of Immunological Methods 32, 297–304 (1980)] can be used.

It is also appropriate to use a polyclonal antiserum and a monoclonal antibody.

One of these antibodies is labeled and the other is coated on a solid phase. The suitable solid phases are those mentioned earlier in this application. Suitable labels are enzymes, e.g. peroxidase, radioactive labels or fluorescence-labels. The preferred solid phase is a plastic bead and the preferred label is horse-radish peroxidase.

The sera sample is then incubated with the solid phase antibody and the labeled antibody. It is possible to treat the sample first with the solid phase antibody and after washing to treat the sample with the labeled antibody. However, it is also possible to treat the sample first with the solid phase antibody and after a certain time with the labeled antibody. Preferably the sample is treated together with the solid phase and the labeled antibody.

After the immunological reaction(s), a washing step may be performed. After washing, the label is determined according to procedures known in the art. In the case where peroxidase is used as the label, the determination is performed with the substrate, e.g., with o-phenylene diamine or with tetramethylbenzidine. The amount of the labeled component is proportional to the amount of the antigen(s) present in the sample.

The methods and assays for the determination and quantification of HIV-1, HIV-2 or of antibodies against HIV-1 or HIV-2 as described above can be conducted in suitable test kits comprising, in a container, a cyclic peptide of the present invention, peptide mixtures or a combination thereof, or antibodies against HIV-1 or HIV-2 elicited by a cyclic peptide or a mixture of cyclic and linear peptides of the present invention.

Panel of Sera Tested

To demonstrate the surprising sensitivity and specificity of the peptides of this invention a panel of sera was tested with illustrative peptides.

O.D. Values were obtained at 450 nm and the blank values measured with the sample dilution buffer were not subtracted.

Samples NEIA-2*2, BBI-1-162 to 168, 87B140, 87L139, 87V103 are all negative for HIV antibodies. Sample LSPQ-S9-1 is an early seroconverter (HIV-1). The series labeled CAP-113 to CAP-120 corresponds to a pool of seven HIV-1 positive plasma samples serially diluted with an HIV-negative plasma. CAP-113 is the pool diluted 50-fold with the HIV-negative plasma; CAP-114 is diluted 100-fold; CAP-115 is diluted 200-fold; etc. Similarly, the series labeled CAP-222 to CAP-230 corresponds to a pool of seven HIV-2 confirmed seropositive plasma samples. CAP-222 is diluted by 50 with an HIV-negative plasma; CAP-223 by 100; etc. Before the assay is done, each sample, including the CAP-series, is further diluted by 50 with the sample dilution buffer. In these tests, the cut-off for seropositivity is defined as the sum of the O.D. value for sample NEIA-2*2 plus 0.100.

Results

The cyclic peptides of the present invention were coated and tested in accordance with the ELISA test described previously. TABLE 2 compares the sensitivity of peptide BCH-87c (586(arginine)) to the sensitivity of peptide BCH-87ck (586(lysine)) and peptide BCH 266 (586(lysine)—585 (lysine)) at progressively higher dilutions of the antibody in the sera samples. It was found that the substitution of a lysine for the arginine at amino acid position 586 increased the sensitivity in detecting HIV-1 antibodies. A further increase in sensitivity was obtained by an additional lysine at position 585. TABLE 3 compares the activity of BCH-87c, BCH-87ck, BCH-266 and BCH-408 at progressively higher dilutions. It is evident from TABLE 3 that peptide BCH-408, wherein an important epitope located at position 606–610 (SGKLI) is repeated at its c-terminus, has superior sensitivity compared to the other peptides.

It was found with the HIV-2 peptides that substituting a lysine for the arginine at amino acid position 578 increased the sensitivity in detecting HIV-2 antibodies. A further increase in sensitivity was obtained by an additional lysine at position 577. TABLE 4 compares the sensitivity of the peptide BCH-202c (578(arginine)) to the sensitivity of peptide BCH-202ck (578(lysine)) and peptide BCH 265 (598 (lysine)—577(lysine)) at progressively higher dilutions of the antibody in the sera samples.

Peptide cocktails were also made to detect a mixture of HIV-1 and HIV-2 antibodies. TABLE 5 illustrates the sensitivity of peptide cocktail mixtures BCH-87c and BCH-202c (arginine) versus BCH-87ck and BCH-202ck (lysine). The peptide cocktail which included the peptides with lysine substituted for arginine have a higher sensitivity in detecting HIV antibodies.

TABLE 2

| Test 314 | HIV-1 O.D. 450 nm | | |
|---|---|---|---|
| Sample ID | BC-87c | BCH-87ck | BCH-266 |
| Dil. Buffer | 0.017 | 0.016 | 0.014 |
| NEIA-2*2 | 0.045 | 0.050 | 0.069 |
| BBI-1-162 | 0.010 | 0.015 | 0.028 |
| BBI-1-169 | 0.095 | 0.090 | 0.138 |
| BBI-1-172 | 0.012 | 0.019 | 0.030 |
| CAP-113 | >2.8 | >2.8 | >2.8 |
| CAP-114 | >2.8 | >2.8 | >2.8 |
| CAP-115 | 1.935 | 2.593 | >2.8 |
| CAP-116 | 1.275 | 1.871 | 2.376 |
| CAP-117 | 0.739 | 1.158 | 1.569 |
| CAP-118 | 0.433 | 0.679 | 0.934 |
| CAP-119 | 0.231 | 0.392 | 0.567 |
| CAP-120 | 0.137 | 0.229 | 0.376 |
| CAP-222 | 0.059 | 0.069 | 0.095 |
| CAP-223 | 0.053 | 0.060 | 0.075 |
| CAP-224 | 0.051 | 0.054 | 0.084 |
| CAP-225 | 0.049 | 0.050 | 0.135 |
| CAP-226 | 0.046 | 0.050 | 0.140 |
| CAP-227 | 0.041 | 0.043 | 0.085 |
| CAP-228 | 0.038 | 0.042 | 0.091 |
| CAP-230 | 0.043 | 0.049 | 0.123 |

TABLE 3

| Test 350 | HIV-1 O.D. 450 | | | |
|---|---|---|---|---|
| Sample ID | BCH-87c | BCH-87ck | BCH-266 | BCH-408 |
| Dil. Buffer | 0.016 | 0.032 | 0.013 | 0.015 |
| NEIA-2*2 | 0.027 | 0.034 | 0.023 | 0.035 |
| 2-87-V-103 | 0.020 | 0.015 | 0.020 | 0.014 |
| 2-87-L-139 | 0.158 | 0.409 | 0.147 | 0.025 |
| 89-D-307 | 0.026 | 0.022 | 0.030 | 0.029 |
| CAP-10 | >2.8 | >2.8 | >2.8 | >2.8 |
| CAP-11 | >2.8 | >2.8 | >2.8 | >2.8 |
| CAP-12 | 2.432 | 2.735 | >2.8 | >2.8 |
| CAP-13 | 1.488 | 1.676 | 2.021 | 2.319 |
| CAP-14 | 0.866 | 1.089 | 1.248 | 1.433 |
| CAP-15 | 0.449 | 0.643 | 0.680 | 0.835 |
| CAP-16 | 0.262 | 0.274 | 0.366 | 0.455 |

TABLE 3-continued

HIV-1

| Test 350 Sample ID | O.D. 450 | | | |
|---|---|---|---|---|
| | BCH-87c | BCH-87ck | BCH-266 | BCH-408 |
| CAP-17 | 0.141 | 0.191 | 0.198 | 0.244 |
| CAP-18 | 0.099 | 0.114 | 0.116 | 0.156 |
| CAP-19 | 0.068 | 0.053 | 0.056 | 0.102 |

TABLE 4

HIV-2

| Test 226 Sample ID | O.D. 450 nm | | |
|---|---|---|---|
| | BC-202c | BCH-202ck | BCH-265 |
| Dil. Buffer | 0.015 | 0.014 | 0.015 |
| NEIA-2*2 | 0.020 | 0.027 | 0.022 |
| 88I-1-162 | 0.018 | 0.033 | 0.059 |
| BBI-1-169 | 0.018 | 0.028 | 0.076 |
| BBI-1-172 | 0.019 | 0.024 | 0.050 |
| CAP-113 | 1.795 | >2.8 | >2.8 |
| CAP-114 | 1.070 | 2.015 | 2.134 |
| CAP-115 | 0.611 | 1.195 | 1.330 |
| CAP-116 | 0.325 | 0.642 | 0.718 |
| CAP-117 | 0.174 | 0.365 | 0.410 |
| CAP-118 | 0.089 | 0.189 | 0.190 |
| CAP-119 | 0.057 | 0.082 | 0.117 |
| CAP-120 | 0.041 | 0.084 | 0.094 |
| CAP-222 | >2.8 | >2.8 | >2.8 |
| CAP-223 | >2.8 | >2.8 | >2.8 |
| CAP-224 | 2.313 | >2.8 | >2.8 |
| CAP-225 | 1.448 | 2.418 | 2.480 |
| CAP-226 | 0.758 | 1.436 | 1.674 |
| CAP-227 | 0.448 | 0.745 | 0.960 |
| CAP-228 | 0.233 | 0.409 | 0.363 |
| CAP-230 | 0.139 | 0.279 | 0.272 |

TABLE 5

HIV-1
Comparative Performance of Two Peptide-Cocktails

| Test 310 Sample ID | O.D. 450 nm | |
|---|---|---|
| | BC-87c BC-202c | BCH-87ck BCH-202ck |
| Dil. Buffer | 0.015 | 0.013 |
| NEIA-2*2 | 0.034 | 0.062 |
| BBI-1-162 | 0.044 | 0.034 |
| BBI-1-163 | 0.032 | 0.042 |
| BBI-1-164 | 0.052 | 0.077 |
| BBI-1-165 | 0.038 | 0.059 |
| BBI-1-166 | 0.045 | 0.081 |
| BBI-1-167 | 0.020 | 0.064 |
| BBI-1-168 | 0.031 | 0.041 |
| 87-B-140 | 0.005 | 0.015 |
| 87-L-139 | 0.025 | 0.068 |
| 87-V-103 | 0.022 | 0.035 |
| CAP-113 | >2.8 | >2.8 |
| CAP-114 | 2.634 | >2.8 |
| CAP-115 | 1.720 | >2.8 |
| CAP-116 | 0.965 | 2.459 |
| CAP-117 | 0.548 | 1.685 |
| CAP-118 | 0.302 | 1.036 |
| CAP-119 | 0.158 | 0.609 |
| CAP-120 | 0.104 | 0.341 |
| CAP-222 | >2.8 | >2.8 |
| CAP-223 | 2.470 | >2.8 |
| CAP-224 | 1.709 | >2.8 |
| CAP-225 | 1.003 | 2.441 |
| CAP-226 | 0.554 | 1.733 |
| CAP-227 | 0.289 | 1.001 |
| CAP-228 | 0.169 | 0.611 |
| CAP-230 | 0.086 | 0.343 |
| LSPQ-S9-1 | 0.123 | 1.273 |
| BBI-A-01 | 0.067 | 0.078 |
| BBI-A-02 | 0.114 | 0.130 |
| BBI-A-03 | 0.180 | 1.069 |
| BBI-A-04 | 2.401 | >2.8 |
| BBI-A-05 | >2.8 | >2.8 |
| BBI-A-06 | >2.8 | >2.8 |
| BBI-A-07 | >2.8 | >2.8 |
| BBI-A-08 | >2.8 | >2.8 |
| BBI-A-09 | >2.8 | >2.8 |
| BBI-C-20 | 0.019 | 0.050 |
| BBI-C-21 | 0.017 | 0.048 |
| BBI-C-22 | 0.030 | 0.121 |
| BBI-C-24 | 0.210 | 1.748 |
| BBI-C-25 | 0.372 | 2.452 |
| BBI-C-26 | 0.374 | 2.353 |

The following illustrates the general procedures for the synthesis and utilization of the peptides of this invention.

Procedure 1

Preparation of Resins Carrying the Nα-FMOC Protected Amino Acid Residue

The desired Nα-FMOC protected amino acid residue in a mixture of methylene chloride ($CH_2Cl_2$) and dimethylformamide (DMF) (4:1) was added to a suspension of p-benzyloxy alcohol resin in $CH_2Cl_2$:DMF (4:1) at 0° C. The mixture was stirred manually for a few seconds and then treated with N,N'-dicyclohexylcarbodiimide (DCC) followed by a catalytic amount of 4-(dimethylamino)pyridine. The mixture was stirred at 0° C. for an additional 30 minutes and then at room temperature overnight. The filtered resin was washed successively with $CH_2Cl_2$, DMF and isopropanol (3 washes each) and finally, with $CH_2Cl_2$. The resin was suspended in $CH_2Cl_2$, chilled in an ice bath and redistilled pyridine was added to the stirred suspension Benzoyl chloride was then also added. Stirring was continued at 0° C. for 30 minutes and then at room temperature for 60 minutes. After filtration, the resin was washed successively with $CH_2Cl_2$, DMF and isopropanol (3 washes each) and finally with petroleum ether (twice) before being dried under high vacuum to a constant weight. Spectrophotometric determination of substitution according to Meienhofer et al. (Int. J. Peptide Protein Res., 13, 35, 1979) indicates the degree of substitution on the resin.

Procedure 2

Coupling of Subsequent Amino Acids

The resin carrying the Nα-FMOC protected first amino acid residue was placed in a reaction vessel of a Biosearch 9600 Peptide Synthesizer and treated as follows:

1) Washed with DMF (4 times for 20 sec. each)
2) Prewashed with a 30% solution of piperidine in DMF (3 min.)
3) Deprotected with a 30% solution of piperidine in DMF (7 min.)

4) Washed with DMF (8 times for 20 sec. each)

5) Checked for free amino groups—Kaiser Test (must be positive)

6) The peptide resin was then gently shaken for 1 or 2 hrs with 8 equivalents of the desired FMOC-protected amino acid and 1-hydroxybenzotriazole and benzotriazol-1-yl-oxy-tris(dimethyl-amino) phosphonium hexafluorophosphate all dissolved in dry redistilled DMF containing 16 equivalents of 4-methylmorpholine.

7) Washed with DMF (6 times for 20 sec. each)

After step 7, an aliquot was taken for a ninhydrin test. If the test was negative, one goes back to step 1 for coupling of the next amino acid. If the test was positive or slightly positive, steps 6 and 7 should be repeated.

The above scheme maybe used for coupling each of the amino acids of the peptides described in this invention. Nα-protection with FMOC may also be used with each of the remaining amino acids throughout the synthesis.

Radiolabeled peptides may be prepared by incorporation of a tritiated amino acid using the above coupling protocol.

After the addition of the last amino acid, the Nα-FMOC of the N-terminal residue is removed by going back to steps 1–7 of the above scheme. The peptide resin is washed with $CH_2Cl_2$ and dried in vacuo to give the crude protected peptide.

Procedure 3

Deprotection and Cleavage of the Peptides From the Resin

The protected peptide-resin was suspended in a 55% solution of trifluoroacetic acid (TFA) in $CH_2Cl_2$, containing 2.5% ethanedithiol and 2.5% anisole. The mixture was flushed with $N_2$ and stirred for 1.5 hours at room temperature. The mixture was filtered and the resin washed with $CH_2Cl_2$. The resin was treated again with 20% TFA in $CH_2Cl_2$ for 5 minutes at room temperature. The mixture was filtered and the resin washed with 20% TFA in $CH_2Cl_2$ and then washed with $CH_2Cl_2$. The combined filtrates were evaporated in vacuo below 35° C. and the residue triturated several times with dry dimethyl ether. The solid was dissolved in 10% aqueous acetic acid and lyophilized to afford the crude product.

The peptides containing arg and cys residues are further deprotected by HF treatment at 0° C. for 1 hour in the presence of anisole and dimethylsulfide. The peptides were extracted with 10% aqueous acetic acid, washed with dimethyl ether and lyophilized to afford the crude peptides.

Procedure 4

Purification of Peptides

The crude peptides were purified by preparative HPLC on a Vydac column (2.5×25 mm) of $C_{18}$ or $C_4$ reverse phase with a gradient of the mobile phase. The effluent was monitored at 220 nm and subsequently by analytical HPLC. Relevant fractions were pooled, evaporated and lyophilized. The identity of the synthetic peptides was verified by analytical reverse phase chromatography and by amino acid analysis.

Procedure 5

Cyclization of Peptides

A solution of potassium ferricyanide (0.01M, pH 7.0) was added slowly to a dilute aqueous solution (0.5 mM) of the linear peptide at pH 7.0. After 24 hours at room temperature, the pH was lowered to 5.0 and the solution treated with ion exchange resin (Bio-Rad Ag-3-X4a, Cl-form) for 30 minutes. The suspension was filtered and the filtrate lyophilized to give the crude cyclic peptide. The peptide was purified by preparative reverse phase HPLC and characterized by amino acid analysis. Proof of cyclicity was obtained by comparing the HPLC mobility of the cyclic peptide with the starting linear peptide by reducing an aliquot of the cyclic peptide back to the linear peptide and also by observing the disappearance of free sulfhydryl groups (Ellman's Test) after the cyclization.

Procedure 6

Conjugation of Peptides to Bovine Serum Albumin or Keyhole Limpet Hemocyanin

Peptides were conjugated to BSA or KLH previously derivatized with either sulfosuccinimidyl 4-(p-maleimidophenyl)butyrate (Sulfo-SMPB) or sulfosuccinimidyl 4-(N-maleimidomethyl)cyclohexane-1-carboxylate (Sulfo-SMCC).

An aqueous solution of sulfo-SMPB or sulfo-SMCC (Pierce Chemicals) was added to a solution of BSA or KLH in 0.02 M sodium phosphate buffer (pH 7.0). The mixture was shaken at room temperature for 45 minutes and the activated carrier immediately applied to a Sephadex G-25 column equilibrated with 0.1M sodium phosphate buffer (pH 6.0) at 4° C.

The fractions of the first peak absorbance (280 nm) corresponding to activated carrier were combined in a round bottom flask to which was added a solution of peptide in 0.05 M sodium phosphate buffer (pH 6.2). The mixture was thoroughly flushed with $N_2$ and incubated overnight at room temperature. The coupling efficiency was monitored using $^3H$-labeled peptide and by amino acid analysis of the conjugate.

Procedure 7

Detection of Antibodies to HIV by an Enzyme Linked Immunosorbent Assay (ELISA)

Each well of the microtiter plate is saturated with 100 μl of a solution containing a peptide or mixture of peptides (5 μg/ml) and left overnight. The wells are emptied and washed twice with a washing buffer (Tris, 0.043M; NaCl, 0.5M; thimerosal, 0.01% w/v; Tween 20, 0.05% v/v; pH 7.4). The wells are then saturated with 0.35 ml of washing buffer for 1 hr. at 37° C. and washed once with the same buffer. Serum samples to be analyzed are diluted with specimen buffer (washing buffer plus casein, 0.05% w/v). The wells are rinsed with washing buffer prior to the addition of the diluted serum sample (0.1 ml). These are left to incubate for 1 hr. at room temperature. The wells are then emptied, washed twice rapidly and then once for two minutes with washing buffer. The conjugate solution (affinity purified goat antibody to human IgG peroxidase labeled, 0.5 mg in 5 ml 50% glycerol) diluted with 1% w/v bovine serum albumin in washing buffer is added to each well (0.1 ml) and incubated for 1 hr. at room temperature. The wells are then emptied and washed twice rapidly with washing buffer and then five times in which the buffer was in contact with the well 2 minutes per washing. The substrate solution (3,3',5,5'-tetramethylbenzidine, 8 mg per ml of DMSO) is diluted with 100 volumes 0.1M citrate-acetate buffer, pH 5.6 containing 0.1% v/v of 30% $H_2O_2$ and added to each well (0.1 ml per well). After 10 minutes the contents of each well is treated with 0.1 ml 2N $H_2SO_4$ and the optical density read at 450 nm. All determinations are done in duplicate.

Procedure 8

Preparation of Peptide Cocktails

Peptide cocktails were prepared by mixing together equal volumes of two peptide solutions each at 10 ug/ml. One cocktail used peptides BCH-87c and BCH-202c and the other cocktail was a mixture of BCH-87ck and BCH-202ck. Each cocktail was used to coat two series of plates as described earlier.

We claim:

1. A purified peptide having the formula

a-x-CSGKLIC-y-f-b wherein:
- a represents the H group which attaches to form the amino terminus or a substituent effective as a coupling agent to make the peptide more useful as an immunodiagnostic reagent without changing its antigenic properties;
- b represents the OH group which attaches to form the carboxy terminus or a substituent effective as a coupling agent to make the peptide more useful as an immunodiagnostic reagent without changing its antigenic properties;
- x is KILAVERYLKDQQLLGIWG;
- y is TTAVPWNA; and
- f is SGKLI.

2. A mixture comprising the following peptides:

a-KILAVERYLKDQQLLGIWGCSGKLICTTAVPWNASGKLI-b and

a-KVTAIEKYLQDQARLNSWCAFRQVCHTTVPWVNDSAFRQV-b wherein:
- a represents the H group which attaches to form the amino terminus or a substituent effective as a coupling agent to make the peptide more useful as an immunodiagnostic reagent without changing its antigenic properties; and
- b represents the OH group which attaches to form the carboxy terminus or a substituent effective as a coupling agent to make the peptide more useful as an immunodiagnostic reagent without changing its antigenic properties.

3. A method for detecting the presence of antibodies to HIV-1, said method comprising contacting an analyte suspected of containing said antibodies with the peptide of claim 1 in a manner and for a time sufficient to allow binding of said antibodies to said peptide, and detecting binding of said antibodies to said peptide.

* * * * *